(12) United States Patent
Allen et al.

(10) Patent No.: US 6,634,499 B2
(45) Date of Patent: Oct. 21, 2003

(54) TRAY FOR MEDICAL INSTRUMENTATION

(75) Inventors: Kraig H. Allen, Warsaw, IN (US);
Thomas J. Bussell, Warsaw, IN (US);
Donald R. Frush, Warsaw, IN (US)

(73) Assignee: Paragon Medical, Pierceton, IN (US)

( * ) Notice: Subject to any disclaimer, the term of this patent is extended or adjusted under 35 U.S.C. 154(b) by 109 days.

(21) Appl. No.: 09/877,221

(22) Filed: Jun. 8, 2001

(65) Prior Publication Data

US 2002/0074253 A1 Jun. 20, 2002

Related U.S. Application Data

(60) Provisional application No. 60/210,554, filed on Jun. 9, 2000.

(51) Int. Cl.⁷ .............................................. B65D 83/10
(52) U.S. Cl. ....................... 206/370; 206/438; 220/533; 422/300
(58) Field of Search ............................ 206/363, 370, 206/372, 373, 438; 220/326, 529, 530, 532, 533; 422/297, 300, 310

(56) References Cited

U.S. PATENT DOCUMENTS

| | | | | |
|---|---|---|---|---|
| 5,284,632 A | * | 2/1994 | Kudla et al. | 206/370 |
| 5,346,677 A | * | 9/1994 | Risk | 206/370 |
| 5,725,097 A | * | 3/1998 | Bettenhausen et al. | 422/300 |
| 5,913,422 A | * | 6/1999 | Cote et al. | 206/370 |
| 6,012,577 A | * | 1/2000 | Lewis et al. | 206/370 |

* cited by examiner

Primary Examiner—Luan K. Bui
(74) Attorney, Agent, or Firm—Botkin & Hall, LLP

(57) ABSTRACT

A tray which includes a floor member having openings formed therein for the passage of sterilization material. A plurality of upright flexible brackets are anchored to the floor and a lid is pivotally connected to the brackets in a manner which allows the lid to be frictionally retained in various positions relative to the underlying floor and brackets.

7 Claims, 7 Drawing Sheets

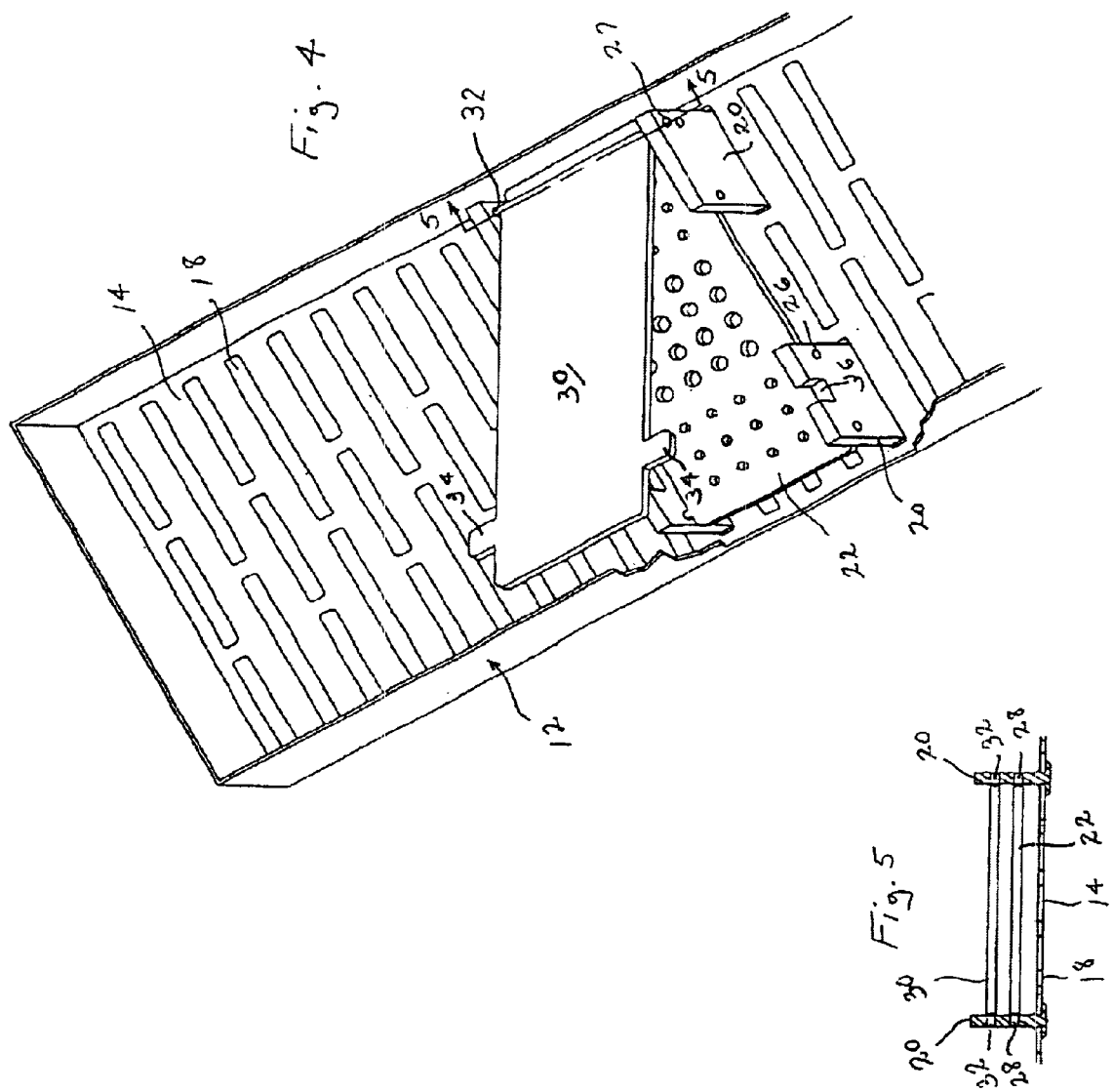

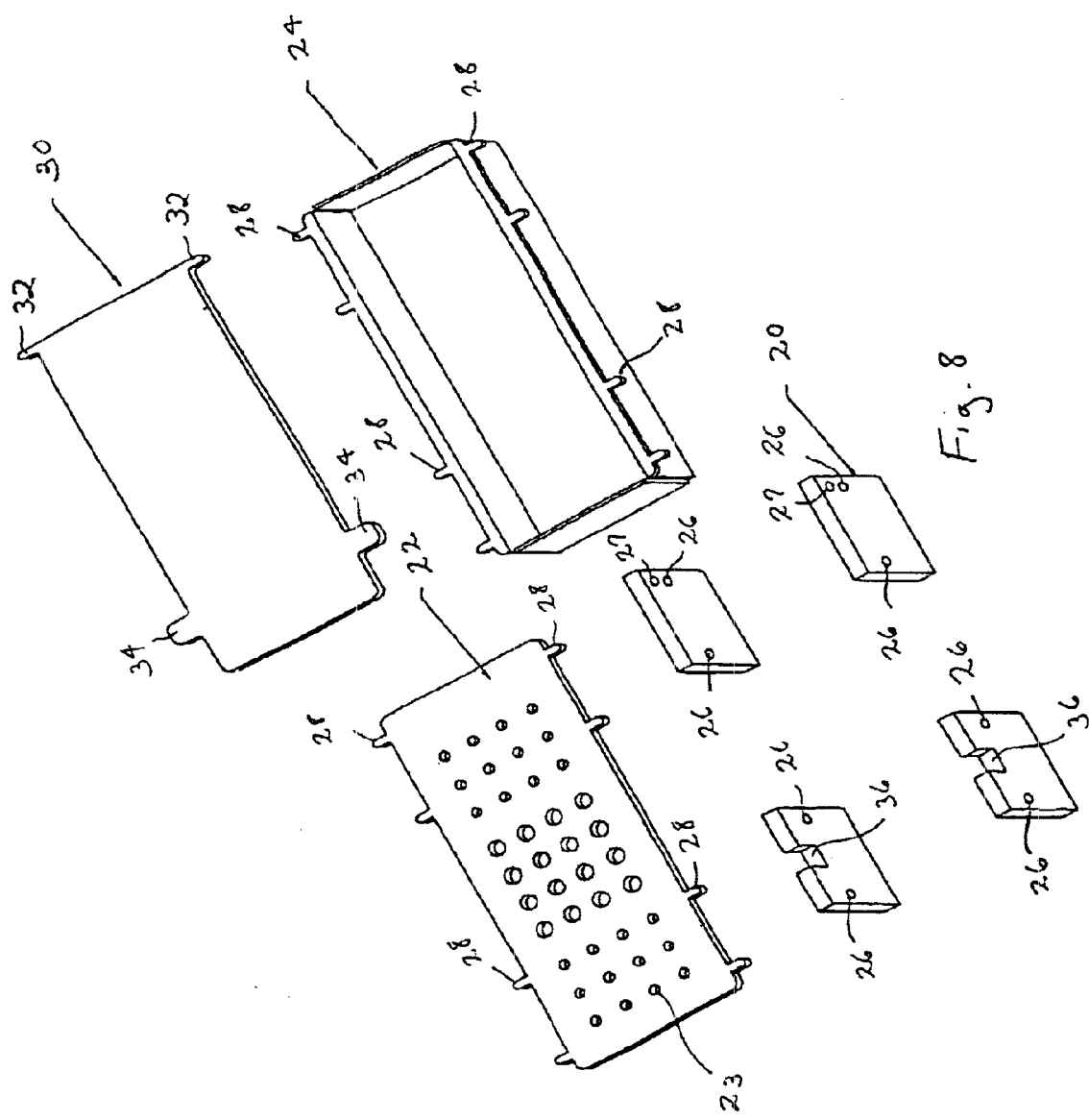

ized material and receiving openings for brackets 20.
TRAY FOR MEDICAL INSTRUMENTATION

CROSS REFERENCE TO RELATED APPLICATION

This is a continuation of provisional application No. 60/210,554 filed Jun. 9, 2000.

SUMMARY OF THE INVENTION

This invention relates to a tray used to contain medical instrumentation and will have specific but not limited to application to a tray used for sterilizing the instrumentation.

Heretofore traditional sterilization trays have had rotative lids used for covering instruments and which rotate either to full open at 180 degrees or to slightly over 90 degrees where they engage stops forming a part of the trays. Lids which open to 180 degrees took up valuable space around the operating or emergency room tables. A tray lid that engaged stops and was positioned slightly over 90 degrees in its open position was vulnerable to contact by the nurses or doctors which sometimes caused the tray to be tipped over with the instrumentation being spilled. In this invention the lid of the tray is retained by flexible silicone brackets which serve to frictionally engage the lid in a manner which allows the lid to be placed in any number of selected open positions. Should the lid be accidentally contacted by a nurse or doctor, it will simply be pivoted either closed or more fully open with no tipping or capitulating of the tray occurring. Additionally, the lid may be very simply removed from tray by flexing the brackets to allow the lid to be disconnected. Also, an instrumentation bin or plate can also be secured to the flexible brackets in an underlying position relative to the lid.

Accordingly, it is an object of this invention to provide a tray for medical instrumentation having one or more lids which can be pivoted into any number or infinite open positions.

Another object of this invention is to provide a tray for medical instrumentation which can be assembled in an efficient and rapid manner.

Still another object of this invention is to provide a medical instrumentation tray which may be used for sterilization and which includes flexible brackets to accommodate bins or plates for the storage of instrumentation.

Other objects of this invention are going to be apparent upon a reading of the following description.

BRIEF DESCRIPTION OF THE DRAWINGS

Preferred embodiments of this invention have been chosen for purposes of illustration and description wherein:

FIG. 4 is a fragmentary perspective view like FIG. 3 and showing the lid in a partially raised fixed position.

FIG. 5 is a fragmentary sectional view as seen along line 5—5 of FIG. 4.

FIG. 8 is a perspective view of the component parts of the tray, namely the brackets, screw plate, bin and lid.

DESCRIPTION OF THE PREFERRED EMBODIMENTS

Figure 1:
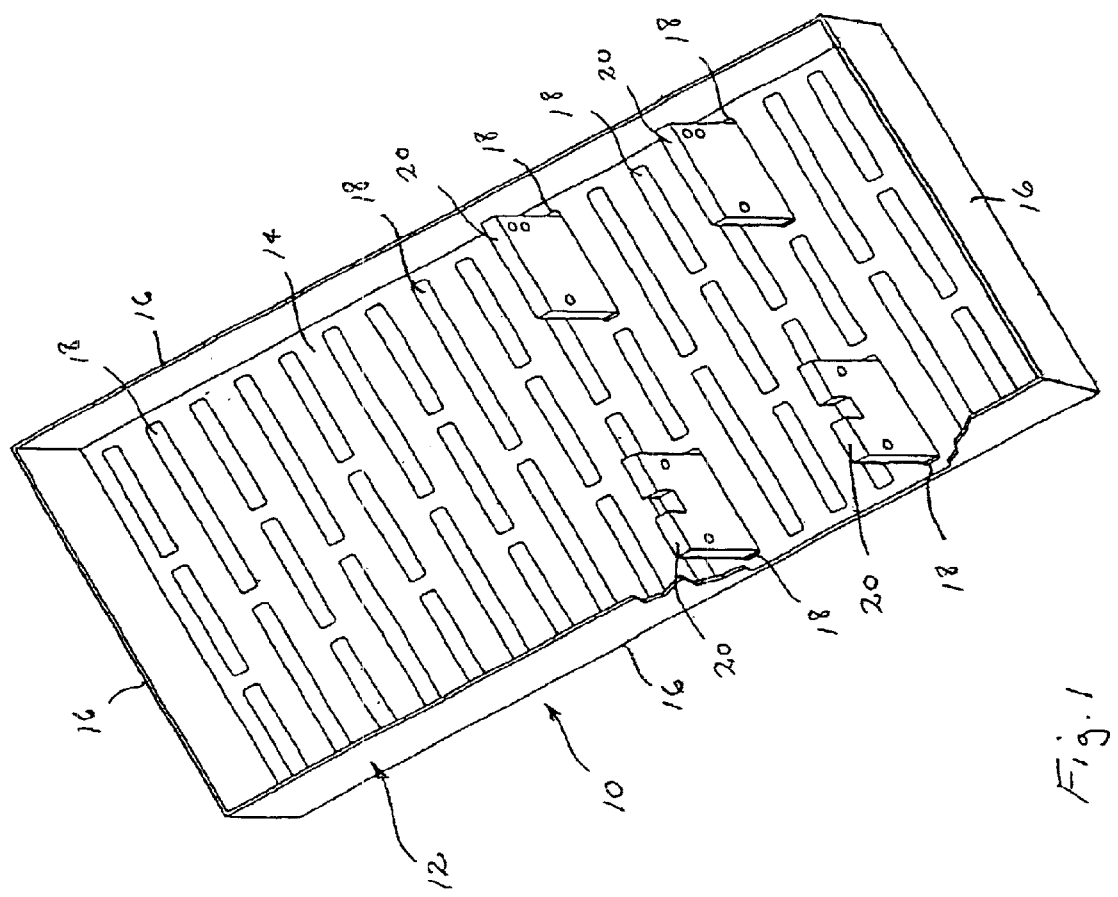
FIG. 1 is a perspective view of a base forming a part of the tray having the flexible brackets anchored to the base and parts broken away for illustrative purposes.
Figure 2:
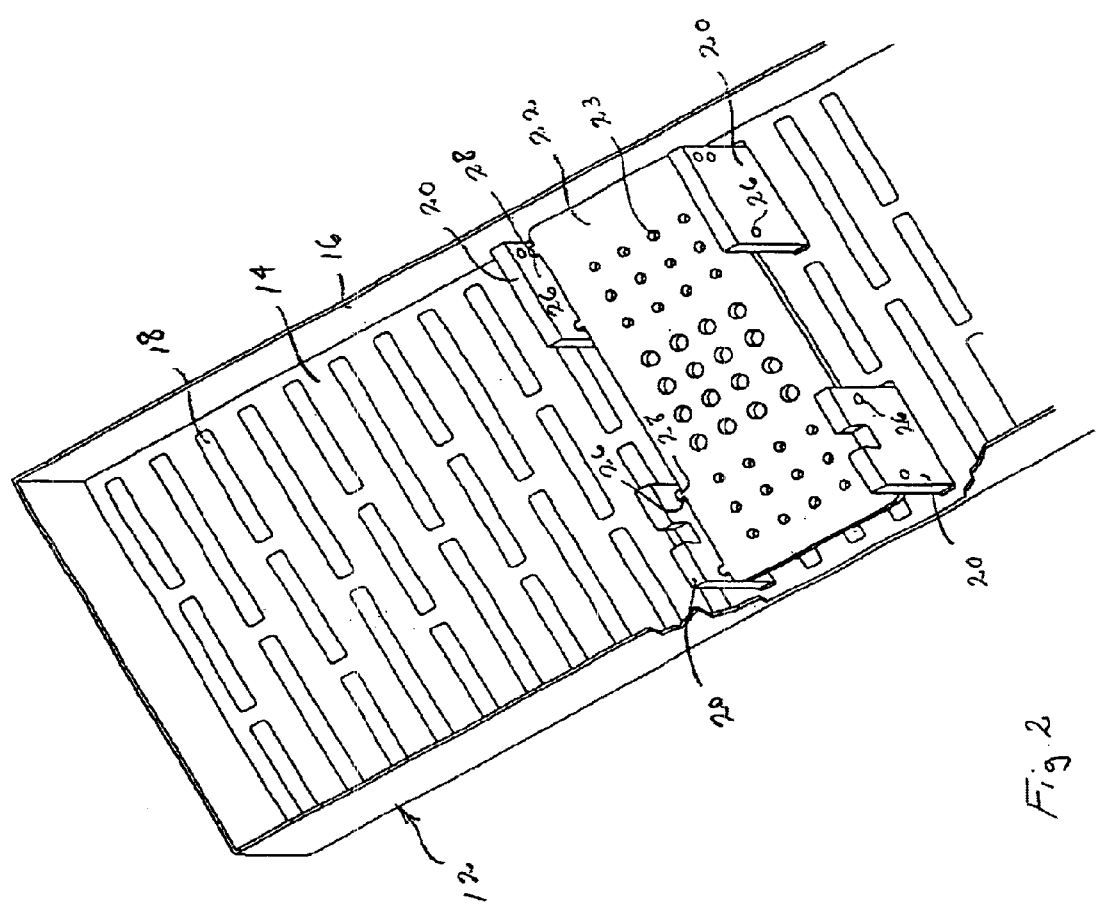
FIG. 2 is a fragmentary perspective view like FIG. 1 and including a screw plate carried by the brackets.
Figure 3:
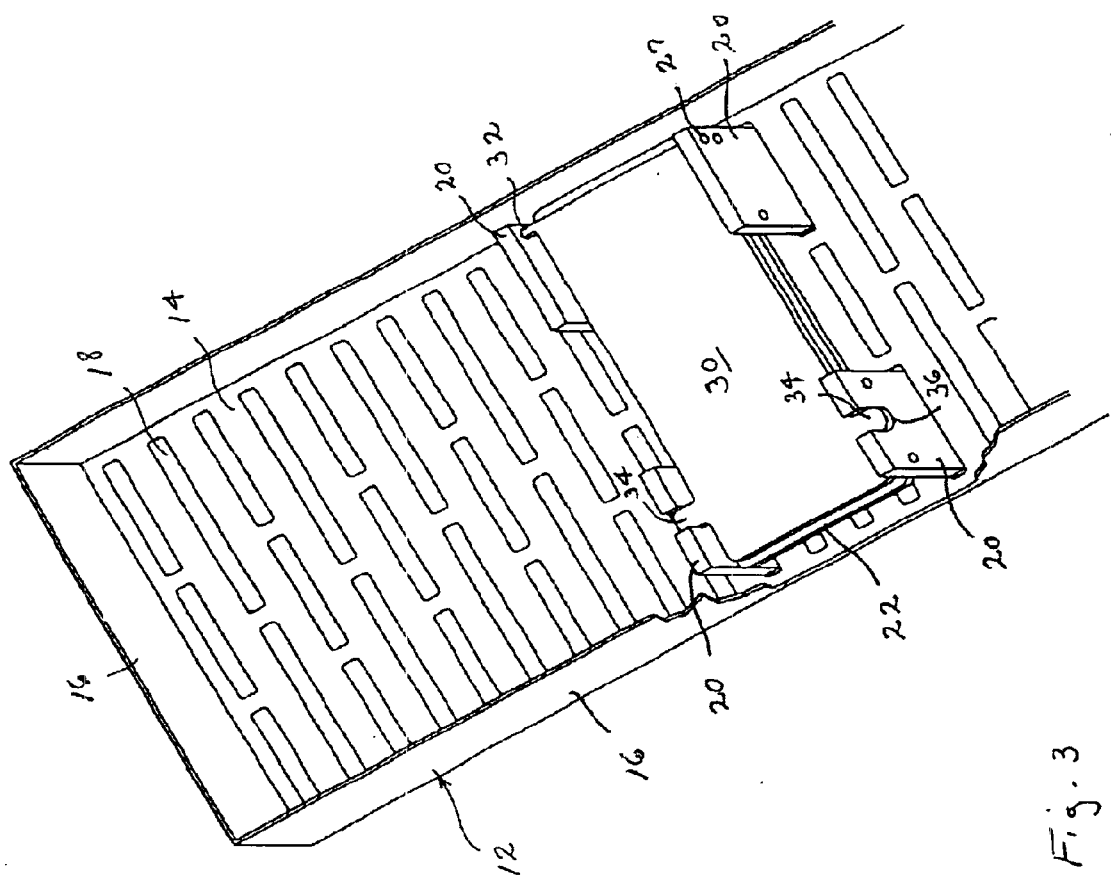
FIG. 3 is a fragmentary perspective view like FIG. 2 and showing a lid pivotally connected to the brackets and overlying the screw plate.
Figure 6:
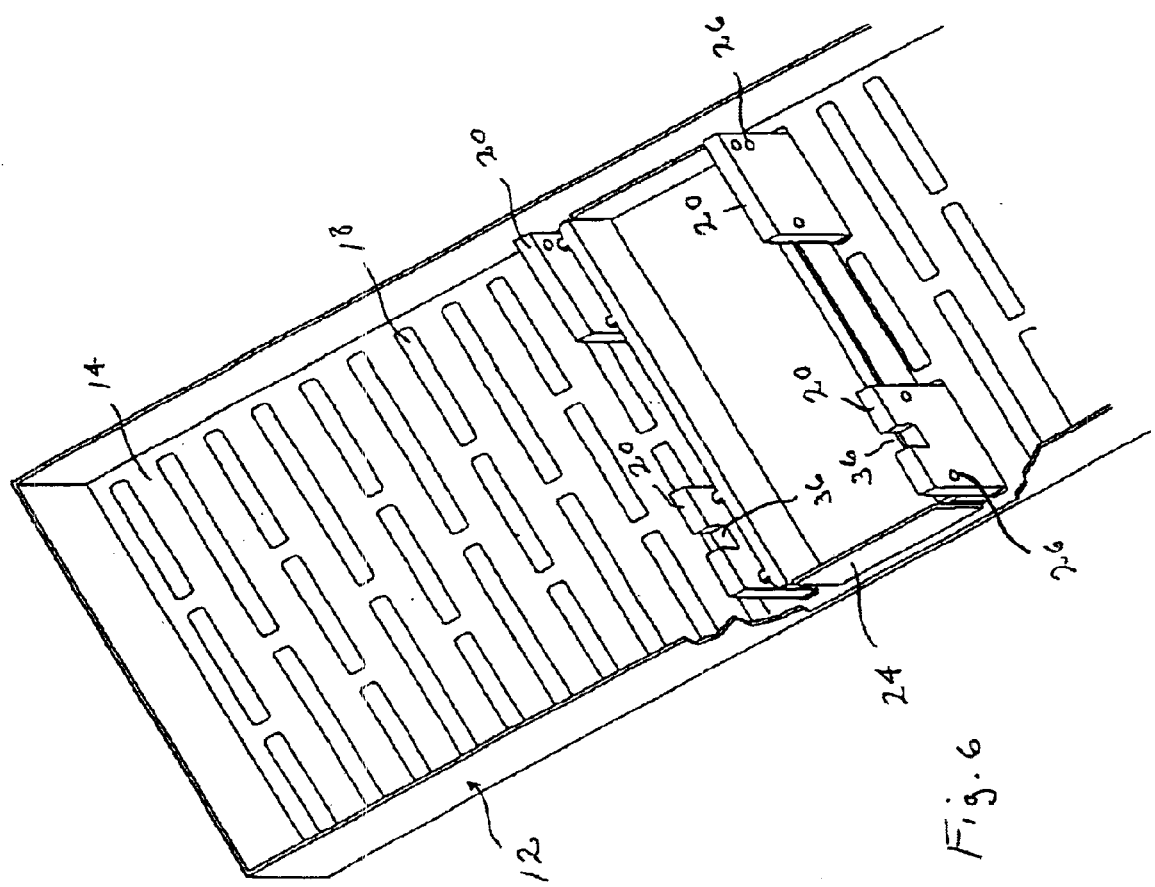
FIG. 6 is a fragmentary perspective view of the base of the instrumentation tray showing a bin connected to and supported by the brackets.

Tray 10 of this invention which is for housing medical devices such as instruments or implants and which may be used as a sterilization tray includes a base 12 having a floor 14 from which four upstanding walls 16 extend to enclose the floor. Floor 14 has a plurality of slotted openings 18 which are used for multiple purposes, such as, ports for the steril Brackets 20 which are preferably of a silicone construction are used to selectively support instrumentation holders such as the screw plate 22 illustrated and the bin 24, also illustrated. For this purpose brackets 20 are provided with openings or recesses 26 at selectively located positions above floor 14. The instrumentation holders, such as plate 22 and bin 24, include outwardly extending tabs 28 which are fitted into openings 26 in the brackets. Brackets 20 are flexible, shape-retaining as well as resilient which allows the brackets to be flexed outwardly in order to accommodate the initial placement of tabs 28 within bracket openings 26. This allows for the simple and easy assembly and disassembly of various types of instrument holders for a given tray. As observed in FIG. 5, brackets 20 are press fitted upwardly into the selected openings 18 in base floor 14 and retained by a snap-fitted, wedge fit. The brackets may be easily removed and repositioned in other selected openings 18 depending upon the type of instrumentation and instrumentation holder the tray is to accommodate. As such, in FIG. 2 plate 22 is shown in a supported and suspended position above floor 14 and in FIG. 6 bin 24 is shown supported and suspended above floor 14.

Figure 7:
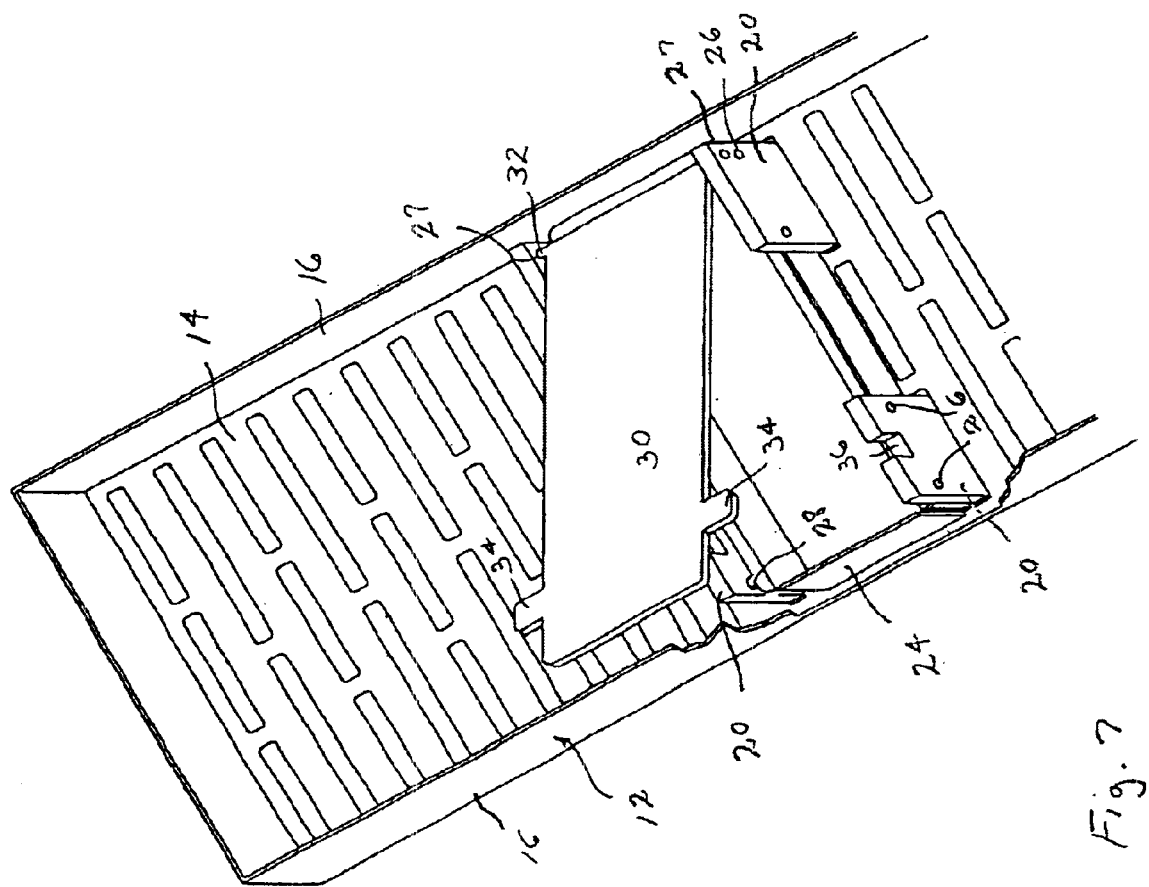
FIG. 7 is a fragmentary perspective view like FIG. 6 and showing a lid pivotally connected to the brackets and fixed in a partially open position over the bin.

A lid 30 is provided to cover the instrumentation or instrument holder. Lid 30 includes at one end oppositely extending trunnions 32 which are inserted into openings or recesses 27 in an opposed set of brackets 20 to cause the lid to rotate relative to the brackets and the underlying instrument holder such as screw plate 22 with its screw receiving openings 23 or bin 24. Trunnions 32 of lid 30 are force-fitted into openings 27 in brackets 20 with the resiliency of the brackets providing a sufficient interference or frictional fit about the received trunnions that the lid 30 may be positioned or stopped in any selected position during its pivotal movement relative to the brackets and the underlying instrument container and floor 14 such as shown in FIGS. 4 and 7. Thus lid 30 may be placed in a fully opened position at approximately 90 degrees relative to floor 14 or any inwardly angled or outwardly angled position. Should the lid be accidentally contacted by a user of the instrument tray, it will simple give in a rotative manner about its axis of rotation defined by trunnions 32 into a more fully closed or more fully opened position without tilting or otherwise disturbing the orientation of the tray and the instruments contained therein. Lid 30 also includes at its free or opposite end a pair of opposed anchor tabs 34 which fit into accommodating slots 36 formed in the underlying brackets 20 in a slight forced-fit with the flexible and resilient bracket accommodating the forceful entry of tabs 34 so as to releasably secure the lid in a closed position.

Base 12, plate 22 and bin 24 may be formed from a metal material or a plastic material. Brackets 20 which are preferably formed from a silicone of medical grade quality. The specific shape and construction of base 12 and the various forms and types of instrument containers can vary depending upon the needs of the user. A cover will also generally be provided for base 12 which is removed during use of the tray to expose the instrumentation.

The invention is not to be limited to the details above given but may be modified within the scope of the appended claims.

What we claim is:

1. A tray for medical instrumentation comprising a floor member, a plurality of upright flexible brackets anchored to said floor member, a lid including trunnion parts, said trunnion parts frictionally engaging two of said brackets in a space relationship from said floor member, said brackets each having a recess therein, each said trunnion part fitted into a said bracket recess, said lid being pivotal about its said trunnion parts within said last two mentioned brackets relative to said floor member, and an instrumentation container having securement parts each engaging a said bracket to fixedly position said container relative to said floor and under said lid.

2. The tray of claim 1 wherein said brackets are of a flexible, shape-retaining resilient composition, each said trunnion part having an interference fit within such said bracket recess to allow selected pivotal orientation of the lid relative to said floor member.

3. The tray of claim 2 wherein said brackets are of a silicone composition.

4. The tray of claim 1 wherein said lid includes anchor parts spaced from said trunnion parts, said lid having a closed position wherein said anchor parts releaseably interlock with another two of said brackets.

5. The tray of claim 1 wherein each said securement part is fitted into a said bracket recess.

6. A tray for medical instrumentation comprising a base having a floor member having openings formed therein for the passage of sterilization material, a plurality of upright flexible shape-retaining resilient brackets anchored to said floor, an instrumentation container having securement parts engaging said brackets to fixedly position said container within said base relative to said floor, a lid pivotally connected to two of said brackets in a spaced relationship from said floor, said lid being pivotal relative to said floor between a closed position overlying said instrumentation container and any of a selected number of raised positions.

7. The tray of claim 6 wherein said brackets each have a recess therein, said securement parts of said instrumentation container each fitted into a said bracket recess, said lid including trunnion parts, said trunnion parts frictionally engaging two of said brackets within other of said bracket recesses.

\* \* \* \* \*